(12) United States Patent
Souza et al.

(10) Patent No.: US 10,611,772 B2
(45) Date of Patent: Apr. 7, 2020

(54) CRYSTALLINE FORM OF RIBOCICLIB SUCCINATE

(71) Applicant: Apotex Inc., Toronto (CA)

(72) Inventors: Fabio E. S. Souza, Mississauga (CA); Bahareh Khalili, Mississauga (CA)

(73) Assignee: Apotex Inc., Toronto, Ontario (CA)

( * ) Notice: Subject to any disclaimer, the term of this patent is extended or adjusted under 35 U.S.C. 154(b) by 0 days.

(21) Appl. No.: 16/454,200

(22) Filed: Jun. 27, 2019

(65) Prior Publication Data

US 2020/0002343 A1 Jan. 2, 2020

Related U.S. Application Data

(60) Provisional application No. 62/693,011, filed on Jul. 2, 2018.

(51) Int. Cl.

| *C07D 487/04* | (2006.01) |
| *C07D 401/14* | (2006.01) |
| *C07D 403/14* | (2006.01) |
| *A61K 31/519* | (2006.01) |
| *A61K 9/20* | (2006.01) |

(52) U.S. Cl.
CPC .............. *C07D 487/04* (2013.01); *A61K 9/20* (2013.01); *C07B 2200/13* (2013.01)

(58) Field of Classification Search
CPC .. C07D 487/04; C07D 401/14; C07D 403/14; A61K 31/519
USPC ........................ 514/265.1; 544/280
See application file for complete search history.

(56) References Cited

U.S. PATENT DOCUMENTS 9,193,732 B2  11/2015  Calienni et al.
9,994,579 B2 * 6/2018  Chen .................... A61K 31/519

2017/0342075 A1  11/2017  Chen et al.
2018/0057498 A1   3/2018  Chen et al.
2018/0071292 A1   3/2018  Gururajan et al.

FOREIGN PATENT DOCUMENTS

| CN | 108245486 A | 7/2018 |
| EP | 3156406 A1 | 4/2017 |
| IN | 201741000072 A | 7/2018 |
| WO | 2012064805 A1 | 5/2012 |
| WO | 2016091221 A1 | 6/2016 |
| WO | 2016166703 A1 | 10/2016 |
| WO | 2018051280 A1 | 3/2018 |
| WO | 2018064797 A1 | 4/2018 |
| WO | 2019019959 A1 | 1/2019 |
| WO | 2019040567 A1 | 2/2019 |
| WO | 2019062854 A1 | 4/2019 |
| WO | 2019111160 A1 | 6/2019 |
| WO | 2019130068 A1 | 7/2019 |
| WO | 2019150181 A1 | 8/2019 |

OTHER PUBLICATIONS

Bernstein, Polymorphism in Molecular Crystals, 2002, pp. 9-10, Oxford University Press, New York.
Porter, "Coating of Pharmaceutical Dosage Forms", Remington the Science and Practice of Pharmacy, 2006, pp. 929-938, Chapter 46, 21st Edition, Lippincott Williams & Wilkins, Philadelphia.
Rudnic et al., "Oral Solid Dosage Forms", Remington the Science and Practice of Pharmacy, 2006, pp. 889-928, Chapter 45, 21st Edition, Lippincott Williams & Wilkins, Philadelphia.
Assessment Report for Kisqali®, European Medicines Agency, Jun. 22, 2017, 121 pages.

* cited by examiner

*Primary Examiner* — Niloofar Rahmani
(74) *Attorney, Agent, or Firm* — The Webb Law Firm

(57) ABSTRACT

The present invention provides a novel crystalline form of Ribociclib succinate, Ribociclib succinate Form APO-I, including Ribociclib succinate, benzyl alcohol and water, compositions thereof, processes for the preparation thereof, and the use of this crystalline form in the treatment of conditions associated with increased CDK4/6 kinase activity, and in particular, cancers, including certain forms of breast cancer.

11 Claims, 1 Drawing Sheet

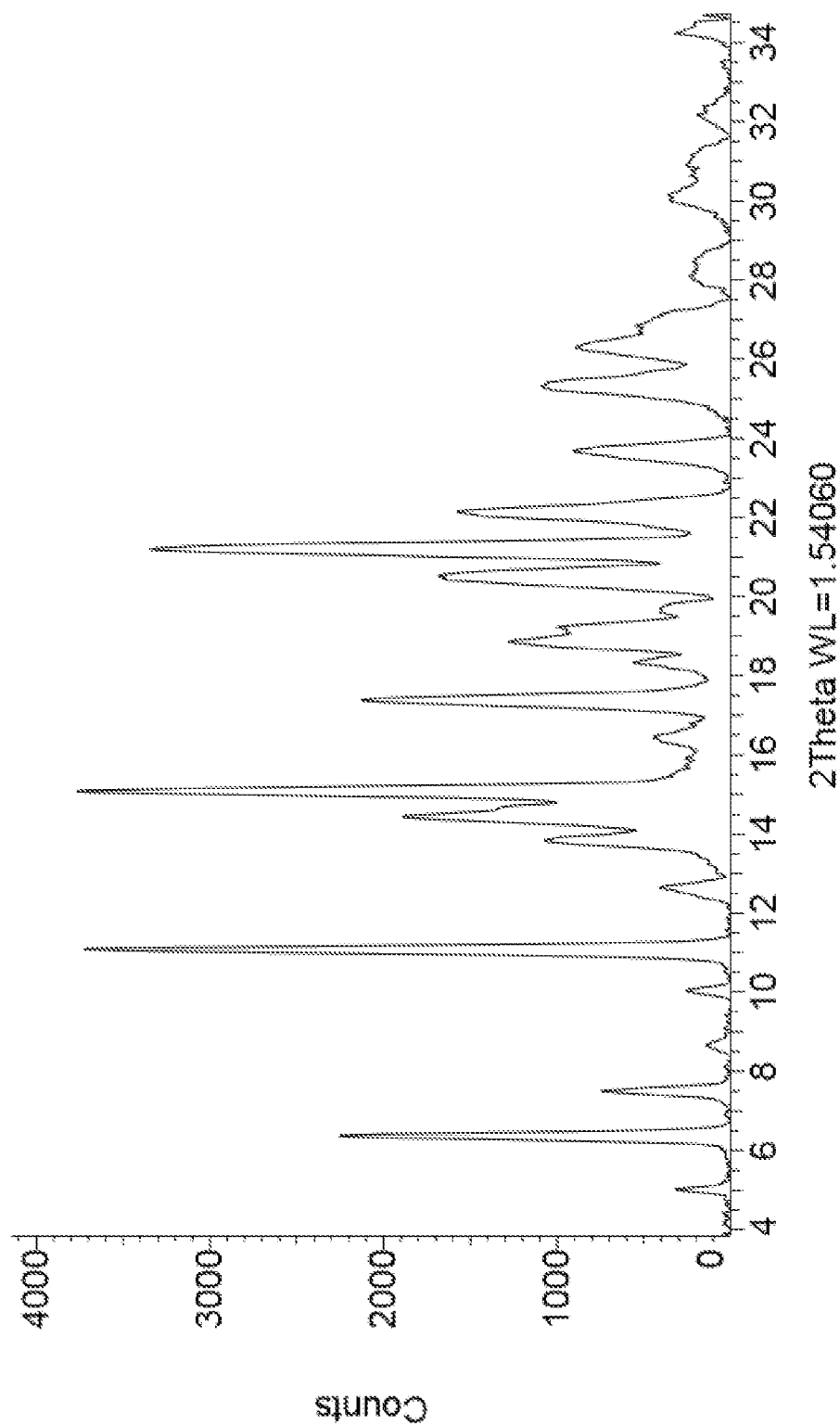

CRYSTALLINE FORM OF RIBOCICLIB SUCCINATE

CROSS-REFERENCE TO RELATED APPLICATION

This application claims the benefit of U.S. Provisional Patent Application No. 62/693,011, filed Jul. 2, 2018, the disclosure of which is hereby incorporated by reference in its entirety.

TECHNICAL FIELD

The present invention is directed to novel crystalline forms of Ribociclib succinate, pharmaceutical compositions containing these forms, processes for their preparation, and their use in the treatment of conditions associated with increased CDK4/6 kinase activity, including certain forms of breast cancer.

BACKGROUND

Ribociclib (1), or 7-cyclopentyl-N,N-dimethyl-2-{[5-(piperazin-1-yl) pyridin-2-yl]amino}-7H-pyrrolo[2,3-d]pyrimidine-6-carboxamide, in the form of a succinate salt, is the active ingredient in KISQALI®, which is indicated, in combination with an aromatase inhibitor, as initial endocrine-based therapy for the treatment of postmenopausal women with hormone receptor (HR)-positive, human epidermal growth factor receptor 2 (HER2)-negative, advanced or metastatic breast cancer.

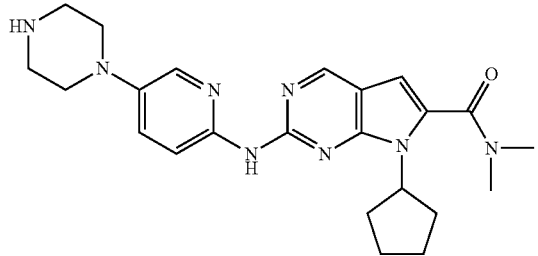

(1)

WO 2012/064805 A1 discloses a 'non-hydrate' form and a hydrate form of Ribociclib succinate. However, the non-hydrate form is hygroscopic and converts to the hydrate form upon exposure to high humidity levels, whereas the hydrate form is reported to have 60 times lower solubility compared to the non-hydrate form. Furthermore, the method of preparation of the hydrate form in WO 2012/064805 A1, by exposure of the non-hydrate form to high humidity, is impractical to execute on commercial scale.

According to the European CHMP Assessment Report for KISQALI® (EMEA/H/C/004213/0000), the drug substance Ribociclib succinate, which by reference to the chemical formula in the report is in the anhydrous form, has both low solubility and moderate permeability, placing it in Class IV of the Biopharmaceutics Classification System (BCS). Of the four BCS Classes, owing to their low solubility and poor permeability, Class IV drug substances present the most challenges to achieving adequate bioavailability.

Furthermore, according to the CHMP report for KISQALI®, the drug substance Ribociclib succinate in the approved tablet exhibits hygroscopicity. Consistent with this hygroscopicity, the CHMP report describes packaging measures typically used for the exclusion of moisture, such as use of 'very tight' quadruple lamination for the storage of the Ribociclib succinate drug substance, and blister packaging for the drug product. Additionally, the coating of KISQALI® tablets comprises polyvinyl alcohol, which, according to WO 2016/166703 A1, is useful as a moisture barrier for Ribociclib succinate tablets.

The solubility of individual crystalline forms of a drug substance in an aqueous environment often correlates to their relative bioavailability since the manner in which the crystalline form dissolves can correspond to the amount of the drug substance that is available to be absorbed into the body, and thereby provide the intended therapeutic effect. One measure of solubility is intrinsic dissolution rate (IDR), which is the dissolution rate of a substance under constant surface area conditions. For low solubility substances such as Ribociclib succinate that are classified as BCS Class IV, higher IDR values can correlate with higher bioavailability following administration. Prediction of the solubility and IDR of an as yet undiscovered crystalline form of a substance is currently not possible.

Different crystalline forms of the same compound may have different crystal packing, thermodynamic, spectroscopic, kinetic, surface and mechanical properties. For example, different crystalline forms may have different stability properties such that a particular crystalline form may be less sensitive to heat, relative humidity (RH) and/or light. Different crystalline forms of a compound may also be more susceptible to moisture uptake, resulting in a potential alteration of physical characteristics of the form such as flowability, density or compressibility, which can lead to problems during formulation/tabletting and/or to changes in dissolution rate of the formulated drug product. For example, unintended absorption of moisture by a hygroscopic crystalline form of a drug substance can alter its compressibility during tabletting, resulting in a softer tablet having a faster dissolution rate following administration. A particular crystalline form may provide more favourable compressibility and/or density properties, thereby providing more desirable characteristics for formulation and/or product manufacturing. Differences in stability between solid forms of a drug may result from changes in chemical reactivity, such as differential oxidation. Such properties may provide for more suitable product qualities, including a dosage form that is more resistant to discolouration when comprised of a specific crystalline form. Particular crystalline forms may also have different solubilities, thereby providing different pharmacokinetic parameters, which allow for specific crystalline forms to be used in order to achieve specific pharmacokinetic targets. Differences in solubility between crystalline forms are particularly relevant for compounds exhibiting low aqueous solubility, such as BCS Class IV drug substances, where even a modest increase in solubility can provide a beneficial enhancement in bioavailability.

Although general approaches to crystalline form screening of active pharmaceutical ingredients are known, it is well established that the prediction of whether any given compound will exhibit polymorphism is not possible. For example, in the case of Ribociclib succinate, which is reported to exist in anhydrous and hydrated crystalline forms, an anhydrous crystalline form can arise even when using an aqueous solvent system. As reported in US 2017/0342075 A1, anhydrous Form I Ribociclib succinate can be prepared from stirring the non-hydrate form of the salt that is described in WO 2012/064805 A1 in a mixture of water and acetonitrile at 50° C. for 48 hours. Accordingly, it is not possible to extend generalities to the number and kinds of crystalline forms that can exist for Ribociclib succinate, or to what methods will be suitable for the preparation of any given crystalline form. Furthermore, prediction of the properties of any unknown crystalline forms, and how they will differ from other crystalline forms of the same compound, remains elusive (Joel Bernstein, *Polymorphism in Molecular Crystals*, Oxford University Press, New York, 2002, page 9).

Due to the classification of Ribociclib succinate as a BCS Class IV drug substance, and the hygroscopicity and/or instability of Ribociclib succinate anhydrous crystalline forms, there exists a need for novel crystalline forms of Ribociclib succinate having improved properties for use in providing drug products containing Ribociclib succinate, and commercially amenable processes for their manufacture.

SUMMARY

The Ribociclib succinate crystalline form of the present invention comprises Ribociclib succinate, benzyl alcohol and water in a 1:1:1 equimolar ratio. Benzyl alcohol has an established safety record, and can therefore safely be used in materials intended for use in the preparation of pharmaceutical compositions for administration to humans or animals. Further, benzyl alcohol has been known to act as a solubilizer for some compounds. Thus, the provision of a crystalline form of Ribociclib succinate comprising benzyl alcohol in addition to water is expected to provide improvements in the solubility of Ribociclib succinate. This is exemplified in the Ribociclib succinate crystalline form of the present invention, which exhibits higher IDR values when compared to the non-hydrate form of Ribociclib succinate described in WO 2012/064805 A1, which is believed to be the form of Ribociclib succinate used in KISQALI® tablets.

The present invention provides a crystalline form of Ribociclib succinate that can be prepared by an efficient and industrially compatible process. Surprisingly, although the solvent system used at the time of initial crystallization included water, a hemi-succinate salt was not produced. This result is in contrast to US 2017/0342075 A1, which reports that a hemi-succinate salt is afforded in the majority of experiments comprising stirring non-hydrate Ribociclib mono-succinate in a solvent comprising water.

Importantly, despite comprising co-crystallized benzyl alcohol and water, the Ribociclib succinate crystalline form of the present invention exhibits form stability at high temperature and high humidity.

Accordingly, in a first aspect of the present invention, there is provided a crystalline form of Ribociclib succinate comprising Ribociclib succinate, benzyl alcohol and water. In a preferred embodiment of the first aspect, the molar ratio of Ribociclib succinate to benzyl alcohol is between approximately 1:0.75 and 1:1.25. In a further preferred embodiment of the first aspect, the molar ratio of Ribociclib succinate to water is between approximately 1:0.75 and 1:1.25. In a more preferred embodiment of the first aspect, the molar ratio of Ribociclib succinate to benzyl alcohol to water is approximately 1:1:1.

In a further preferred embodiment, the crystalline form of the first aspect of the invention is characterized by a weight loss as determined by thermal gravimetric analysis (TGA) of between about 2% and about 3% in the temperature range of about 40° C. to about 90° C. In a more preferred embodiment, the weight loss as determined by TGA is between about 2.5% and about 2.8% in the temperature range of about 40° C. to about 90° C. In another preferred embodiment, the crystalline form of the first aspect of the invention is characterized by a weight loss as determined by TGA of between about 15% and about 17% in the temperature range of about 95° C. to about 195° C. Most preferably, the crystalline form of the first aspect of the invention is characterized by a weight loss as determined by TGA of between about 2% and about 3% in the temperature range of about 40° C. to about 90° C., and between about 15% and about 17% in the temperature range of about 95° C. to about 195° C.

In a second aspect of the present invention, there is provided a crystalline form of Ribociclib succinate, APO-I, comprising Ribociclib succinate, benzyl alcohol and water, characterized by a PXRD diffractogram comprising peaks, expressed in degrees 2θ (±0.2°), at 6.4°, 11.1° and 15.1°. In a preferred embodiment of the second aspect, the PXRD diffractogram further comprises at least three peaks, expressed in degrees 2θ (±0.2°), selected from the group consisting of: 5.0°, 7.5°, 13.9°, 14.5°, 17.4°, 18.9°, 20.5°, 21.2°, 22.1° and 23.7°. In a further preferred embodiment of the second aspect, the PXRD diffractogram further comprises peaks, expressed in degrees 2θ (±0.2°), at 5.0°, 7.5°, 13.9°, 14.5°, 17.4°, 18.9°, 20.5°, 21.2°, 22.1° and 23.7°. Preferably, the crystalline form of the second aspect of the invention provides a PXRD diffractogram comprising peaks in substantially the same positions (±0.2° 2θ) as those shown in FIG. 1. In a further preferred embodiment of the second aspect, the molar ratio of Ribociclib succinate to benzyl alcohol to water is approximately 1:1:1.

In a third aspect of the present invention, there is provided a pharmaceutical composition comprising a crystalline form of Ribociclib succinate according to the first or second aspects of the invention, and one or more pharmaceutically acceptable excipients. Preferably, the pharmaceutical composition is in the form of a solid dosage form. Most preferably, the pharmaceutical composition is a tablet.

In a fourth aspect of the present invention, there is provided a use of a crystalline form of Ribociclib succinate according to the first or second aspects of the invention, or the pharmaceutical compositions of the third aspect of the invention, in the treatment of conditions associated with increased CDK4/6 kinase activity. In a preferred embodiment of the fourth aspect, the condition associated with increased CDK4/6 kinase activity is cancer. In a further preferred embodiment of the fourth aspect, the cancer is hormone receptor (HR)-positive, human epidermal growth factor receptor 2 (HER2)-negative, advanced or metastatic breast cancer. In a further preferred embodiment of the fourth aspect, the Ribociclib succinate is used in combination with an aromatase inhibitor, preferably Letrozole.

In a fifth aspect of the present invention, there is provided a process for the preparation of the crystalline form of Ribociclib of the first or second aspects of the invention, comprising treating a solution comprising Ribociclib succinate or Ribociclib and succinic acid, benzyl alcohol and water with a C3-C6 alkyl ester. In a preferred embodiment of the fifth aspect, the C3-C6 alkyl ester is selected from the group consisting of methyl acetate, ethyl acetate, isopropyl acetate, isobutyl acetate and n-butyl acetate. Preferably, the C3-C6 alkyl ester is n-butyl acetate. In a further preferred embodiment of the fifth aspect, the molar ratio of Ribociclib succinate or Ribociclib to benzyl alcohol used in the process is between approximately 1:35 and approximately 1:55. In another preferred embodiment of the fifth aspect, the molar ratio of Ribociclib succinate or Ribociclib to water used in the process is between approximately 1:10 and approximately 1:20. Most preferably, the molar ratio of Ribociclib succinate or Ribociclib to benzyl alcohol used in the process is between approximately 1:35 and approximately 1:55, and the molar ratio of Ribociclib succinate or Ribociclib to water used in the process is between approximately 1:10 and approximately 1:20.

Other aspects and features of the present invention will become apparent to those ordinarily skilled in the art upon review of the following description of specific embodiments of the invention in conjunction with the accompanying FIGURES.

BRIEF DESCRIPTION OF THE DRAWINGS

Embodiments of the present invention are described, by way of example only, with reference to the attached FIGURE.

FIG. 1 is a representative PXRD diffractogram of Ribociclib succinate Form APO-I as prepared in Example 1.

DETAILED DESCRIPTION

The Ribociclib succinate crystalline form of the present invention comprises Ribociclib succinate that has crystallized with benzyl alcohol and water. Importantly, with respect to the use of this crystalline form in the preparation of pharmaceutical compositions, benzyl alcohol is included in both the U.S. Food & Drug Administration's (FDA's) Everything Added to Food in the United States (EAFUS) list, and the Inactive Ingredient Database (IID). The EAFUS list contains ingredients added directly to food that the FDA has either approved as food additives, or has listed or affirmed as being GRAS (Generally Recognized As Safe). The IID list provides information on inactive ingredients present in FDA-approved drug products. Once an inactive ingredient has appeared in an approved drug product for a particular route of administration, the inactive ingredient is not considered new, and may require a less extensive review the next time it is included in a new drug product. Also of importance to the present invention is that benzyl alcohol is known to act as a solubilizer for some compounds. Thus, the provision of a crystalline form of Ribociclib succinate comprising Ribociclib succinate, benzyl alcohol and water is expected to provide improvements in the solubility of Ribociclib succinate, which has been classified according to the BCS as a poorly soluble drug. As shown in Example 3, the Ribociclib succinate crystalline form of the present invention exhibits improvements in its IDR when compared to the non-hydrate form of Ribociclib succinate described in WO 2012/064805 A1.

The Ribociclib succinate crystalline form of the present invention exhibits differences in properties when compared to the known crystalline forms of Ribociclib succinate. Properties that differ between the invention and known crystalline forms of Ribociclib succinate include crystal packing properties such as molar volume, density and hygroscopicity; thermodynamic properties such as melting point and solubility; kinetic properties such as dissolution rate and chemical/polymorphic stability; surface properties such as crystal habit/particle morphology; and/or mechanical properties such as hardness, tensile strength, compactibility, tableting, handling, flow, and blending.

Furthermore, the Ribociclib succinate crystalline form of the present invention exhibits stability under conditions of high temperature and high humidity. As reported in WO 2012/064805 A1 and US 2017/0342075 A1, anhydrous forms of Ribociclib succinate show hygroscopicity at high humidities and/or undergo hydration and form conversion. This behavior introduces risk into the handling, storage and formulation of the drug substance, wherein specialized packaging and formulation alterations may be necessary to ensure quality and consistency, which can add to the cost and complexity of manufacturing the commercial drug product. In contrast, the crystalline form of the present invention, which comprises both benzyl alcohol and water that have co-crystallized with Ribociclib, was unchanged following open exposure to conditions of 40° C./75% RH for at least 4 weeks.

Further, the present invention provides a crystalline form of Ribociclib succinate that can be prepared by an efficient and industrially compatible process. Surprisingly, the crystalline form of the present invention can be prepared from a solvent mixture comprising water, despite reports that stirring Ribociclib mono-succinate in aqueous systems affords Ribociclib hemi-succinate, presumably due to the solubilisation of succinic acid. Importantly, in addition to benzyl alcohol and water, the preparation of the crystalline form of the present invention uses Class 3 solvents established by the ICH (International Council for Harmonisation of Technical Requirements for Pharmaceuticals for Human Use) as having low toxicity.

Depending on the manner in which the crystalline forms of the present invention are prepared, and the methodology and instrument used for PXRD analysis, the intensity of a given peak observed in a PXRD diffractogram of the crystalline form may vary when compared to the same peak in the representative PXRD diffractogram provided in FIG. 1. Thus, differences in relative peak intensities between peaks in a PXRD diffractogram for a given crystalline form may be observed when compared to the relative peak intensities of the peaks in the representative PXRD diffractogram of FIG. 1. Any such differences may be due, in part, to the preferred orientation of the sample and its deviation from the ideal random sample orientation, the preparation of the sample for analysis, and the methodology applied for the analysis. Such variations are known and understood by a person of skill in the art, and any such variations do not depart from the invention disclosed herein.

In addition to the differences in relative peak intensities that may be observed in comparison to the representative PXRD diffractogram provided in FIG. 1, it is understood that individual peak positions may vary between ±0.2° 2θ from the values observed in the representative PXRD diffractograms provided in FIG. 1 for the crystalline form of the invention, or listed in Table 1. Such variations are known and understood by a person of skill in the art, and any such variations do not depart from the invention disclosed herein.

Further, depending on the instrument used for X-ray analysis and its calibration, uniform offsets in the peak position of each peak in a PXRD diffractogram of greater that 0.2° 2θ may be observed when compared to the representative PXRD diffractogram provided in FIG. 1. Thus, PXRD diffractograms of the crystalline form of the present invention may, in some circumstances, display the same relative peak positions as observed in the representative PXRD diffractogram provided in FIG. 1, with the exception that each peak is offset in the same direction, and by approximately the same amount, such that the overall PXRD diffractogram is substantially the same in appearance as the PXRD diffractogram of FIG. 1, with the exception of the uniform offset in peak positions. The observation of any such uniform peak shift in a PXRD diffractogram does not depart from the invention disclosed herein given that the relative peak positions of the individual peaks within the PXRD diffractogram remain consistent with the relative peak positions observed in the PXRD diffractogram of FIG. 1.

As used herein, the term 'crystalline form' refers to a substance with a particular arrangement of molecular components in its crystal lattice, and which may be identified by physical characterization methods such as PXRD. As used herein, the term crystalline form is intended to include single-component and multiple-component crystalline forms. Single-component forms of Ribociclib succinate, such as those known in the art, consist solely of Ribociclib succinate in the repeating unit of the crystal lattice. Multiple-component forms of Ribociclib succinate, such as those of the present invention, include crystalline forms of Ribociclib succinate wherein one or more other molecules are also incorporated into the crystal lattice with Ribociclib succinate.

Multi-component crystalline forms comprising more than one type of molecule may have some variability in the exact molar ratio of their components depending on the conditions used for their preparation. For example, a molar ratio of components within a multi-component crystalline form provides a person of skill in the art information as to the general relative quantities of the components of the crystalline form. In many cases, the molar ratio may vary by ±25% from a stated range. With respect to the present invention, a molar ratio of 1:1 should be understood to include the ratios 1:0.75 and 1:1.25, as well as all of the individual ratios in between.

As used herein, the term "room temperature" refers to a temperature in the range of 20° C. to 25° C.

As used herein, when referring to water content, the term "weight percentage" (wt %) refers to the ratio: weight water/(weight water+weight Ribociclib succinate+weight benzyl alcohol), expressed as a percentage.

When describing the embodiments of the present invention there may be a common variance to a given temperature or time that would be understood or expected by the person skilled in the art to provide substantially the same result. For example, when reference is made to a particular temperature, it is to be understood by the person skilled in the art that there is an allowable variance of ±5° C. associated with that temperature. When reference is made to a particular time, it is to be understood that there is an allowable variance of ±10 minutes when the time is one or two hours, and ±1 hour when longer periods of time are referenced.

In one embodiment of the present invention, there is provided a new crystalline form of Ribociclib succinate, Ribociclib succinate Form APO-I, comprising Ribociclib succinate, benzyl alcohol and water. Preferably, in Ribociclib succinate Form APO-I, the molar ratio of Ribociclib to benzyl alcohol to water is approximately 1:1:1.

Ribociclib succinate Form APO-I can be characterized by a PXRD diffractogram comprising, among other peaks, characteristic peaks, expressed in degrees 2θ (±0.2°), at 6.4°, 11.1° and 15.1°. Preferably, the PXRD diffractogram further comprises at least three peaks, expressed in degrees 2θ (±0.2°), selected from the group consisting of 5.0°, 7.5°, 13.9°, 14.5°, 17.4°, 18.9°, 20.5°, 21.2°, 22.1° and 23.7°. More preferably, the PXRD diffractogram further comprises peaks, expressed in degrees 2θ (±0.2°), at 5.0°, 7.5°, 13.9°, 14.5°, 17.4°, 18.9°, 20.5°, 21.2°, 22.1° and 23.7°. PXRD studies of capped and uncapped samples of Ribociclib succinate Form APO-I maintained in a 40° C./75% RH stability chamber for at least 4 weeks showed that no change in the crystalline form occurred.

An illustrative PXRD diffractogram of Ribociclib succinate Form APO-I, as prepared in Example 1, is shown in FIG. 1. A peak listing, comprising representative peaks from the PXRD diffractogram in FIG. 1, and their relative intensities, is provided in Table 1. Although illustrative of the PXRD diffractogram that is provided for the Ribociclib succinate Form APO-I of the present invention, the relative intensities of the peaks are variable. Thus, depending on a particular sample, the prominence or relative intensity of the peaks observed may differ from those in the illustrative PXRD diffractogram and peak listing.

TABLE 1

Relative peak intensities of Ribociclib Succinate Form APO-I from FIG. 1

| Angle (2θ) | Relative intensity (%) |
|---|---|
| 5.02 | 8.4 |
| 6.38 | 59.8 |
| 7.50 | 19.7 |
| 8.66 | 3.8 |
| 10.05 | 6.8 |
| 11.09 | 98.8 |
| 12.66 | 10.6 |
| 13.85 | 28.4 |
| 14.45 | 50.2 |
| 15.08 | 100.0 |
| 16.47 | 11.7 |
| 17.38 | 56.5 |
| 18.33 | 14.8 |
| 18.86 | 34.0 |
| 19.22 | 26.5 |
| 19.66 | 10.7 |
| 20.53 | 44.7 |
| 21.20 | 88.8 |
| 22.13 | 41.8 |
| 23.68 | 24.0 |
| 25.30 | 28.8 |
| 26.30 | 23.7 |

As described in Examples 1 and 2, Ribociclib succinate Form APO-I can be prepared by preparing a solution of Ribociclib succinate in benzyl alcohol and water, preferably at room temperature; adding an anti-solvent, preferably a C3-C6 alkyl ester selected from the group consisting of methyl acetate, ethyl acetate, isopropyl acetate, isobutyl acetate and n-butyl acetate, and most preferably n-butyl acetate; and maintaining the mixture at a suitable temperature, preferably at room temperature, preferably for at least 30 minutes, and more preferably two hours. Preferably, the solution of Ribociclib succinate is prepared by dissolving either Ribociclib succinate or Ribociclib and succinic acid in benzyl alcohol and water, preferably wherein the molar ratio of Ribociclib succinate (or Ribociclib) to benzyl alcohol is between approximately 1:35 and approximately 1:55, and the molar ratio of Ribociclib succinate (or Ribociclib) to water is between approximately 1:10 and approximately 1:20. Filtration of the suspension formed following the addition of anti-solvent, and drying the filtered material, optionally in vacuo and/or at elevated temperature, provides Ribociclib succinate Form APO-I having a PXRD diffractogram consistent with FIG. 1.

In a further embodiment of the invention, there is provided a pharmaceutical composition of a crystalline form of Ribociclib succinate comprising Ribociclib succinate, benzyl alcohol and water with one or more pharmaceutically acceptable excipients. Preferably, the pharmaceutical composition is a solid dosage form suitable for oral administration, such as a capsule, tablet, pill, powder or granulate. Most preferably, the pharmaceutical composition is a tablet. Preferably, the pharmaceutical composition provides a dose of Ribociclib succinate that is equivalent to the 200 mg of Ribociclib succinate found in KISQALI® drug products.

Suitable pharmaceutically acceptable excipients are preferably inert with respect to the crystalline form of Ribociclib succinate of the present invention, and may include, for example, one or more excipients selected from binders such as lactose, starches, modified starches, sugars, gum acacia, gum tragacanth, guar gum, pectin, wax binders, microcrystalline cellulose, methylcellulose, carboxymethylcellulose, hydroxypropyl methylcellulose, hydroxyethyl cellulose, hydroxypropyl cellulose, copolyvidone, gelatine, polyvinylpyrrolidone (PVP) and sodium alginate; fillers or diluents such as lactose, sugar, starches, modified starches, mannitol, sorbitol, inorganic salts, cellulose derivatives (e.g., microcrystalline cellulose, cellulose), calcium sulphate, xylitol and lactitol; disintegrants such as croscarmellose sodium, crospovidone, polyvinylpyrrolidone, sodium starch glycollate, corn starch, microcrystalline cellulose, hydroxypropyl methylcellulose and hydroxypropyl cellulose; lubricants such as magnesium stearate, magnesium lauryl stearate, sodium stearyl fumarate, stearic acid, calcium stearate, zinc stearate, potassium benzoate, sodium benzoate, myristic acid, palmitic acid, mineral oil, hydrogenated castor oil, medium-chain triglycerides, poloxamer, polyethylene glycol and talc; and dispersants or solubility enhancing agents, such cyclodextrins, glyceryl monostearate, hypromellose, meglumine, Poloxamer, polyoxyethylene castor oil derivatives, polyoxyethylene stearates, polyoxylglycerides, povidone, and stearic acid. Other excipients including preservatives, stabilisers, anti-oxidants, silica flow conditioners, antiadherents or glidants may be added as required. Other suitable excipients and the preparation of solid oral dosage forms is well known to person of skill in the art, and is described generally, for example, in Remington The Science and Practice of Pharmacy 21$^{st}$ Edition (Lippincott Williams & Wilkins: Philadelphia; 2006; Chapter 45).

Optionally, when the pharmaceutical compositions are solid dosage forms, the solid dosage forms may be prepared with coatings, such as enteric coatings and extended release coatings, using standard pharmaceutical coatings. Such coatings, and their application, are well known to persons skilled in the art, and are described, for example, in Remington The Science and Practice of Pharmacy 21$^{st}$ Edition (Lippincott Williams & Wilkins: Philadelphia; 2006; Chapter 47).

EXAMPLES

The following non-limiting examples are illustrative of some of the aspects and embodiments of the invention described herein.

The Ribociclib succinate used as a starting material in the following example was consistent with Ribociclib succinate non-hydrate form, which is reported in WO 2012/064805 A1. However, other polymorphic forms are equally suitable as starting material, provided complete dissolution of the form occurs when preparing the novel crystalline form of Ribociclib succinate of the present invention.

PXRD Analysis:

PXRD diffractograms were recorded on a Bruker D8 Discover powder X-ray diffractometer (Bruker-AXS, Karlsruhe, Germany). The generator was a Micro-focus X-ray source (IMSTube: Cu tube with 1.54060 Å) with a voltage of 50 kV and current of 1.00 mA, using a divergence slit of 0.3 mm and collimator of 0.3 mm. For each sample, one frame was collected using a still scan with a Pilatus 3R-100 kA detector at the distance of 154.72 mm from the sample. Raw data were evaluated using the program EVA (Bruker-AXS, Karlsruhe, Germany).

Example 1: Preparation of Ribociclib Succinate Form APO-I

To Ribociclib succinate (500 mg, 0.90 mmol) was added benzyl alcohol (4.5 mL, 43 mmol) and the mixture was stirred at room temperature until dissolved. Water (0.25 mL, 13.9 mmol) was then added and stirring was continued to provide a single phase, followed by slow addition of n-butyl acetate (25 mL). The resulting suspension was stirred for two hours and the resulting solid was collected by filtration, washed with heptane (2×10 mL) and dried in vacuo at room temperature for 16 hours to afford Ribociclib succinate Form APO-I as a pale yellow solid (563 mg, 83% yield) having the PXRD diffractogram shown in FIG. 1. $^1$H NMR analysis of the solid (DMSO-d$_6$) showed a molar ratio of Ribociclib succinate:benzyl alcohol of approximately 1:1. Karl Fischer (KF) analysis of the sample showed water content of 2.9 wt %, which is consistent with a molar ratio of Ribociclib succinate:water of approximately 1:1. TGA (25-360° C. @ 10° C./min; 85 mL/min N$_2$ flow) of the sample showed a first weight loss of 2.5% between 40° C. and 90° C., and a second weight loss of 15.8% between 95° C. and 195° C., which is consistent with a crystalline form comprising an approximate 1:1:1 ratio of Ribociclib succinate:benzyl alcohol:water.

$^1$H-NMR of Ribociclib succinate Form APO-I (DMSO-d$_6$, 300 MHz) δ: 1.56-1.72 (br m, 2H), 1.90-2.06 (br m, 4H), 2.33 (s, 4H), 2.37-2.49 (br m, 2H), 2.98-3.11 (br m, 10H), 3.12-3.22 (m, 4H), 4.49 (s, 2H), 4.73 (quin, J=8.9 Hz, 1H), 6.61 (s, 1H), 7.19-7.27 (m, 1H), 7.28-7.35 (m, 4H), 7.45 (dd, J=2.9, 9.1 Hz, 1H), 8.02 (d, J=2.9 Hz, 1H), 8.17 (d, J=9.1 Hz, 1H), 8.77 (s, 1H), 9.38 (s, 1H)

Example 2: Preparation of Ribociclib Succinate Form APO-I

Ribociclib (193 mg, 0.44 mmol) and succinic acid (51 mg, 0.43 mmol) were dissolved in a mixture of benzyl alcohol (2.2 mL, 21.2 mmol) and water (0.125 mL, 6.94 mmol). Following dropwise addition of n-butyl acetate (12.5 mL), a precipitate formed. After stirring for approximately 30 minutes, the solids were collected by filtration, washed with heptane (2×3 mL) and dried in vacuo for 16 hours at room temperature to afford Ribociclib succinate Form APO-I as a white solid (285 mg, 97% yield) having a PXRD diffractogram consistent with FIG. 1.

Example 3: Comparative Intrinsic Dissolution Testing

Intrinsic dissolution rate (IDR) measurements were performed using a Wood apparatus. Samples were prepared by compressing 400 mg sample at 1.5 metric tons for 1 minute. A dissolution medium consisting of 900 mL 0.01 N HCl buffer, and rotation speed of 75 rpm, was used for each experiment. Results are provided in Table 2.

TABLE 2

Comparative intrinsic dissolution rates for the crystalline
form of the invention with the non-hydrate form of
Ribociclib succinate described in WO 2012/064805 A1

| Form | Intrinsic Dissolution Rate (mg min$^{-1}$ cm$^{-2}$) |
| --- | --- |
| Ribociclib succinate non-hydrate form (Prior Art) | 1.9520 |
| Ribociclib succinate Form APO-I | 8.3417 |

What is claimed is:

1. A crystalline form of Ribociclib succinate comprising Ribociclib succinate, benzyl alcohol and water that is characterized by a PXRD diffractogram comprising peaks, expressed in degrees 2θ (±0.2°), at 6.4°, 11.1° and 15.1°, and at least three further peaks selected from the group consisting of: 5.0°, 7.5°, 13.9°, 14.5°, 17.4°, 18.9°, 20.5°, 21.2°, 22.1° and 23.7°.

2. The crystalline form of claim 1, that is characterized by a PXRD diffractogram comprising peaks, expressed in degrees 2θ (±0.2°), at 5.0°, 6.4°, 7.5°, 11.1°, 13.9°, 14.5°, 15.1° 17.4°, 18.9°, 20.5°, 21.2°, 22.1° and 23.7°.

3. A pharmaceutical composition comprising the crystalline form of Ribociclib succinate according to claim 1, and one or more pharmaceutically acceptable excipients.

4. The pharmaceutical composition of claim 3, wherein the pharmaceutical composition is a tablet.

5. A process for the preparation of the crystalline form of Ribociclib succinate according to claim 1, comprising treating a solution comprising Ribociclib succinate or Ribociclib and succinic acid, benzyl alcohol and water with a C3-C6 alkyl ester.

6. The process of claim 5, wherein the C3-C6 alkyl ester is selected from the group consisting of methyl acetate, ethyl acetate, isopropyl acetate, isobutyl acetate and n-butyl acetate.

7. The process of claim 6, wherein the C3-C6 alkyl ester is n-butyl acetate.

8. The process of claim 7, wherein the molar ratio of Ribociclib succinate or Ribociclib to benzyl alcohol used in the process is between approximately 1:35 and approximately 1:55.

9. The process of claim 8, wherein the molar ratio of Ribociclib succinate or Ribociclib to water used in the process is between approximately 1:10 and approximately 1:20.

10. The crystalline form of claim 1, wherein the molar ratio of Ribociclib to benzyl alcohol to water is approximately 1:1:1.

11. The crystalline form of claim 1, characterized by a weight loss as determined by thermal gravimetric analysis of between about 2% and about 3% in the temperature range of about 40° C. to about 90° C.

* * * * *